United States Patent [19]

Arneric et al.

[11] Patent Number: 5,272,155
[45] Date of Patent: Dec. 21, 1993

[54] (+)-2-METHYLPIPERIDINE AS MODULATOR OF CHOLINERGIC SYSTEMS

[75] Inventors: Stephen P. Arneric, Lindenhurst; Michael W. Decker, Mundelein, both of Ill.

[73] Assignee: Abbott Laboratories, Abbott Park, Ill.

[21] Appl. No.: 802,584

[22] Filed: Dec. 5, 1991

[51] Int. Cl.⁵ .................... A61K 31/445; A61K 31/44
[52] U.S. Cl. ..................................... 514/315; 514/343
[58] Field of Search ............................... 514/315, 343

[56] References Cited

U.S. PATENT DOCUMENTS 3,035,977  5/1962  Abood ................................. 514/315

OTHER PUBLICATIONS

Chemical Abstracts (109: 50124h) 1988.

*Primary Examiner*—Frederick E. Waddell
*Assistant Examiner*—Kevin E. Weddington
*Attorney, Agent, or Firm*—Richard A. Elder; Steven F. Weinstock; Edward H. Gorman, Jr.

[57] ABSTRACT

Pharmaceutical compositions comprising a therapeutically effective amount of (+) 2-methylpiperidine and a pharmaceutically-acceptable carrier or diluent, as well as to a method of treating cognitive, neurological and mental disorders, which are characterized by decreased cholinergic function in humans and lower mammals, by administration of (+)2-methylpiperidine, optionally with a nicotinic agonist.

5 Claims, 2 Drawing Sheets

(+)-2-METHYLPIPERIDINE AS MODULATOR OF CHOLINERGIC SYSTEMS

TECHNICAL FIELD

This invention relates to (+)-2-methylpiperidine which is a specific modulator of the neuronal nicotinic cholinergic receptor and is therefore useful in the treatment and prevention of cognitive, neurological and mental disorders which are characterized by decreased cholinergic function.

BACKGROUND OF THE INVENTION

The compound (±)-2-methylpiperidine has a high degree of specificity in enhancing the binding of nicotine in the rat brain (Sloan, J. W. et al., *J. Med. Chem.* 1985, 28, 1245); specifically, the (+)isomer of (±)2-methylpiperidine enhances the binding of nicotinic ligands to rat brain receptor sites (Sloan, J. W. et al., *Life Sci.* 1985, 37:1367). However, neither of these Sloan et al references suggests that (+)-2-methylpiperidine affects cerebral circulation or cognitive function. It has now been found that (+)-2-methylpiperidine has the ability to enhance nicotinic neurotransmission, either alone or by co-administration with a known nicotinic agonist. This finding has enabled a therapeutically-useful agent having diminished potential side-effects to be produced.

SUMMARY OF THE INVENTION

The present invention is directed to pharmaceutical compositions comprising a therapeutically-effective amount of (+) 2-methylpiperidine or a pharmaceutically-acceptable acid addition salt thereof. This invention is also directed to a method of treating cognitive, neurological and mental disorders, which are characterized by decreased cholinergic function in humans and lower mammals, by administration of (+) 2-methylpiperidine, either alone or with a known nicotinic agonist.

DETAILED DESCRIPTION OF THE INVENTION

Figure 1A:
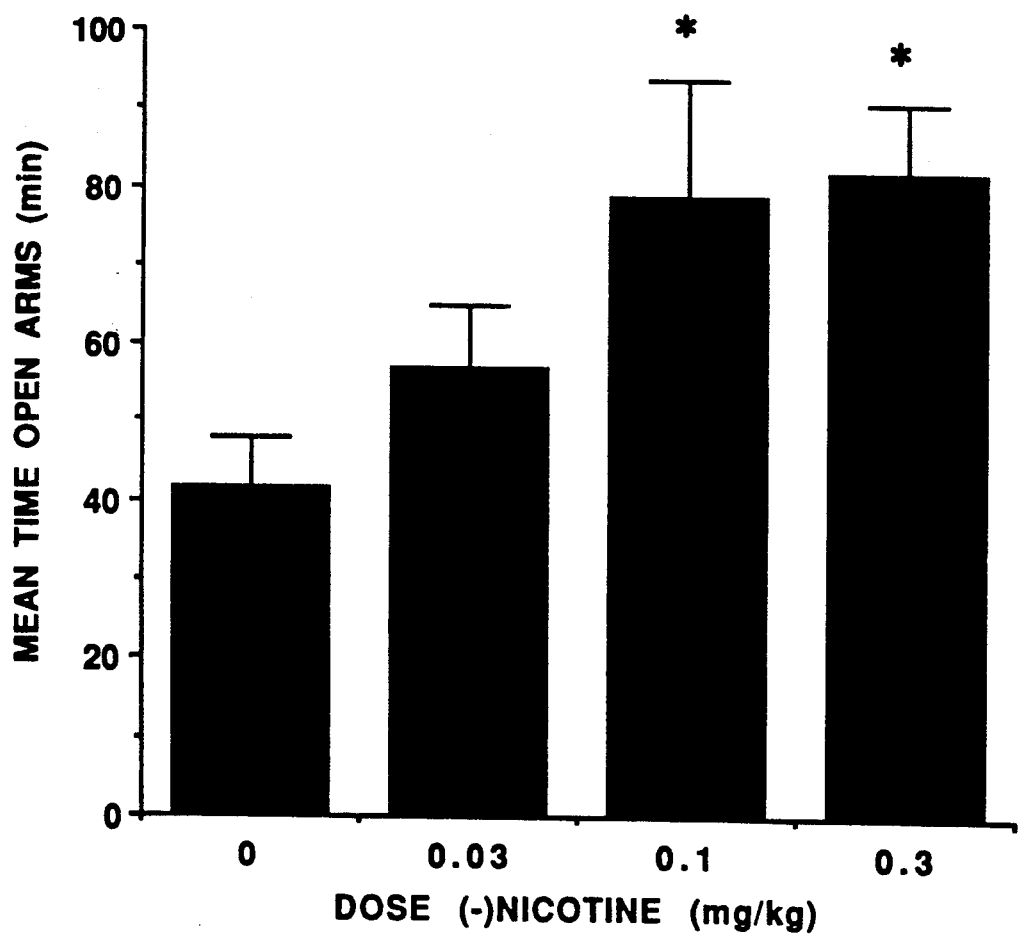
FIG. 1A is a graph of time mice spend in the open arms of the elevated-plus maze (a conflict test that probes anxiolytic activity) as a function of the dose of (−)nicotine administered to the mice. Values are mean ±S.E.M. of n=8; *p<0.05 from saline control.

The instant invention is directed to pharmaceutical compositions comprising a therapeutically-effective amount of (+) 2-methylpiperidine which modulate cortical cholinergic neurotransmission and, therefore, are useful in the treatment of cognitive disorders or neurological and mental illnesses characterized by dysfunction of the cholinergic system. Such diseases include presenile and senile dementia, Alzheimer's Disease age-associated mental impairment, schizophrenia, Parkinson's disease, tardive dyskinesia, hyperkinesia, mania, stroke, attentional deficit disorders, acute confusion disorders, anxiety disorders and anxiety associated with drug dependence withdrawal or cessation (e.g., associated with cigarette or alcohol dependence).

The compound (+) 2-methylpiperidine, may be prepared by resolution of reacemic (±) 2-methylpiperidine, according to the procedures described by Sloan, J. W. et al., *Life Sci.* 1985, 37:1367.

Compounds of the instant invention were confirmed to be cholinergic agonists/modulators capable of interacting with the cholinergic system using an initial screen demonstrating that (+)2-methylpiperidine modulates the cholinergic basal forebrain. The ability of the compounds of the invention to modulate nicotinic receptor-activated behaviors or physiology was demonstrated in vivo using the following protocols.

Differentiation of Properties of (+) and (−) Isomers of 2-Methylpiperidine: In Vivo Determination of Nicotinic Modulatory Action Affecting Basal Forebrain Neurotransmission Previous studies suggest that activation of neurons arising from the cholinergic basal forebrain to the cerebral cortex will elicit an increase in cortical cerebral blood flow (CBF) by a mechanism that is mediated by a nicotinic receptor (Linville and Arneric, *Neurobiology of Aging* 1991, 12(5): 503–510). Methods for surgical preparations of rats for electrical stimulation of brain and measurement of cortical CBF are detailed by Linville and Arneric (1991).

Intravenous (iv) administration of (+) 2-methylpiperidine ((+)2-MP) and (−)2-MP (0.1–3.0 mg/kg) were examined for their effect on mean arterial pressure (MAP), resting CBF and increases in cortical CBF elicited by electrically stimulating the BF (≈25 Hz; 100 uA; 10 sec. train). Low concentrations of (+)2-MP were effective in enhancing resting CBF and the BF-elicited CBF response (Table 1 & 2). No remarkable effects on mean arterial pressure (MAP) were observed (Table 3). In contrast, (−)2-MP had no ability to enhance there nicotinically-mediated effects at all.

TABLE 1

| | Resting Cortical CBF | |
|---|---|---|
| | % of Resting CONTROL | |
| Dose: mg/kg, iv | (+)2-MP (N = 5 rats) | (−)2-MP (N = 3 rats) |
| 0 | 100 (10) | 100 (13) |
| 0.1 | 126 (15) | 99 (32) |
| 0.3 | 133 (22) | 86 (29) |
| 1.0 | 146 (28) | 74 (27) |
| 3.0 | 140 (27) | 70 (30) |

Values are the mean (SEM).

TABLE 2

| | BF-Elicited CBF Response | |
|---|---|---|
| | % of Resting Cortical CBF | |
| Dose: mg/kg, iv | (+)2-MP (N = 5 rats) | (−)2-MP (N = 3 rats) |
| 0 | 153 (11) | 130 (8) |
| 0.1 | 203 (21) | 113 (30) |
| 0.3 | 222 (20) | 101 (28) |
| 1.0 | 222 (23) | 88 (26) |
| 3.0 | 220 (19) | 81 (30) |

Values are the mean (SEM).

TABLE 3

| | Mean Arterial Pressure (M A P (mmHg)) | |
|---|---|---|
| Dose: mg/kg, iv | (+2)-MP (N = 5 rats) | (−)2-MP (N = 3 rats) |
| 0 | 76 (3) | 90 (6) |
| 0.1 | 82 (6) | 78 (4) |
| 0.3 | 87 (5) | 83 (4) |
| 1.0 | 92 (7) | 80 (8) |
| 3.0 | 87 (7) | 73 (4) |

Values are the mean (SEM).

These data indicate that low concentrations of (+) 2-methylpiperidine, but not (−)2-methylpiperidine, effectively act as a putative positive allosteric modulator of the neuronal nicotinic cholinergic receptor, since both spontaneous activity, which affects resting cerebral blood flow, as well as electrically-evoked cerebral blood flow response were enhanced by administration of (+)-2MP. Moreover, (+) 2-methylpiperidine has no overt on blood pressure.

In Vivo Determination to Facilitate the Anxiolytic Action of Nicotine

The mouse elevated-plus maze is a conflict test that probes anxiolytic activity (Lister, *Pyschopharmacology*, 1987, 92:180). It is based on the fact that exposure of mice to an elevated open arm leads to an avoidance response considerably stronger than that evoked by exposure to an enclosed arm.

The apparatus required to perform this test is made of plexiglass and consists of two open arms (17×8 cm) and two enclosed arms (17×8×15 cm) extending from a central platform (8×8 cm). It is mounted on an opaque plexiglass base rising 39 cm above the floor. Mice are released on one of the open arms and the time spent in the open and enclosed arms is recorded during a 5 min. test period. The time spent in open arms is increased in a dose-related way after injection of known anxiolytic drugs like diazepam.

Figure 1B:
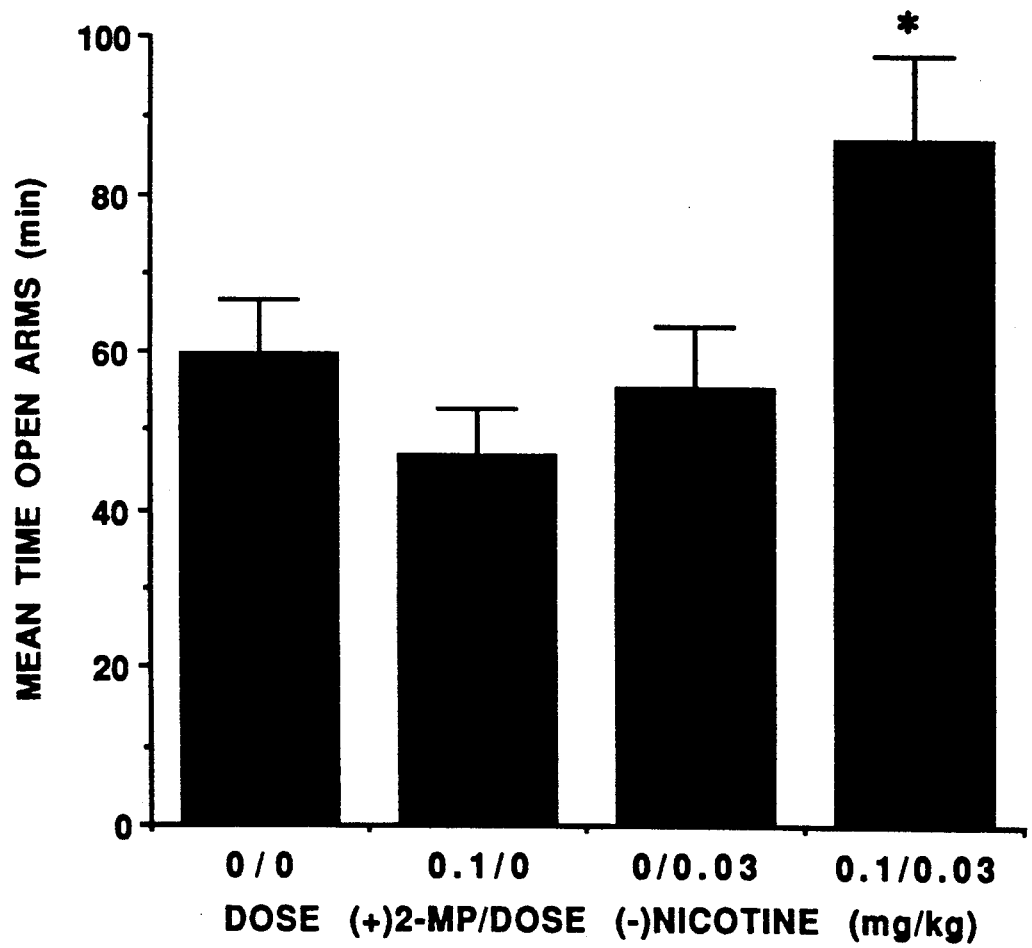
FIG. 1B is a graph of time mice spend in the open arms of the elevated-plus maze as a function of the administration of (+)2-methylpiperidine (0.1 mg/kg) or (−)nicotine administered separately or in combination. Values are means±S.E.M. of n=8; *p<0.05 (0.03 mg/kg) from saline control.

FIG. 1A demonstrates the effect of (−)nicotine on a conflict situation evaluated in the elevated plus-maze task. CD1 mice (n=8 per group) received systemic (−)nicotine injections (0, 0.03, 0.1 or 0.3 mg/kg, IP) fifteen minutes before they were allowed to explore the plus-maze for a 5 minute test period. Nicotine (0.1 and 0.3 mg/kg, $p<0.05$) induced a significant increase in the time spent by the mice in the open arms (a measure of anxiolytic effect) as compared to saline-injected mice. (+)2-Methylpiperidine (0.1 mg/kg, IP) given 5 min. prior to (−)nicotine was able to enhance the anxiolytic activity of a non-effective dose of (−)nicotine (FIG. 1B).

These data support the idea that appropriate doses of (+)2-methylpiperidine can also enhance the beneficial effectiveness of known nicotinic agonists.

In Vivo Activity to Facilitate Habituation

Adult male CD1 mice (n=8/group) were injected with (+)2-methylpiperidine (0, 1.0, 3.0 or 10.0 mg/kg, i.p.) immediately prior or 60 min. prior to placement in automated activity monitors (Omnitech, Columbus, Ohio). These enclosures, measuring 40×40×42 cm, are equipped with a series of photocells and generate measurements of a variety of locomotor activities.

(+)2-Methylpiperidine caused a dose-related enhancement of the habituation process normally seen with mice (FIG. 1), suggesting that the animals "learned" the novel environment at a faster rate. The significan drug-by-time interaction ($p<0.02$) decrement in locomotor activity seen post drug injection was not related to non-specific impairment or sedation, since pretreatment of the animals with 0, 3.0 or 10.0 mg/kg (+)2-methylpiperidine sixty min. prior did not significantly decrease the high level of locomotor activity seen the first 10 min. after introduction to the novel environment [Saline=3680±169; (+)2-MP, 3.0 mg/kg=3402±164; (+)2-MP, 10 mg/kg=3349±126 activity counts].

These data suggest that (+)2-methylpiperidine facilitates habituation, a rudimentary form of learning and memory.

In Vivo Side-Effect Profile

Undesireable side-effects such as hypothermia, and acute toxicity were also assessed.

A. Hypothermia

Adult male CD1 mice (n=5-7/group) were injected with (+)2-methylpiperidine (0, 10 or 100 mg/kg, i.p.) and rectal temperatures were assessed (YSI Model 43 TA) 15 min. later. (+)2-Methylpiperidine was without effect at this time (Table 4), as well as 60 and 120 minutes later (data not shown). In contrast, (−)nicotine significantly lowered temperature following both 0.3 and 1.0 mg/kg, i.p. (Table 5) and produced a greater hypothermic response than did a 10 or 100-fold higher dose of (+)2-methylpiperidine.

TABLE 4

| Effects of (+)2-Methylpiperidine on Rectal Temperatures | | |
|---|---|---|
| | Temperature (°C.) | |
| | Baseline | 15 min. later |
| Saline | 38.5 ± 0.1 | 38.3 ± 0.1 |
| (+)2-Methylpiperidine | | |
| 10 mg/kg | 38.2 ± 0.1 | 38.2 ± 0.1 |
| 100 mg/kg | 38.3 ± 0.1 | 38.2 ± 0.2 |

Values are Means ± S.E.M.

In addition, (+)2-methylpiperidine (1 and 10 mg/kg, i.p.) did not potentiate the hypothermic response to (−)nicotine when given 3 min. prior (Table 5). In fact, the hypothermic response of the low dose of (−)nicotine (0.3 mg/kg) was actually attenuated, whereas the higher dose of (−)nicotine was unaffected by (+)2-methylpiperidine (Table 5).

TABLE 5

| Combined Effects of (−)Nicotine and (+)2-Methylpiperidine on Rectal Temperatures | | |
|---|---|---|
| Pretreatment {mg/kg} | Treatment {mg/kg} | Temperature (°C.) |
| Saline | Saline | 38.3 ± 0.1 |
| Saline | (−)nicotine {0.3} | 36.9 ± 0.2* |
| (+)2-MP {1.0} | (−)nicotine {0.3} | 37.8 ± 0.2 |
| (+)2-MP {10.0} | (−)nicotine {0.3} | 37.5 ± 0.3 |
| Saline | (−)nicotine (1.0) | 36.5 ± 0.6* |
| (+)2-MP {0.1} | (−)nicotine {1.0} | 36.0 ± 0.7* |
| (+)2-MP {10.0} | (−)nicotine {1.0} | 36.5 ± 0.5* |

Values are means ±S.E.M.; * values are statistically decreased from saline control, $p<0.05$; (+)-2-methylpiperidine (mandelic acid salt). (−)Nicotine was given as the base.

In general, (+)2-MP produced more benign side-effects than did (−)nicotine and did not facilitate the undesirable side-effects of a nicotinic agonist such as (−)nicotine.

B. Toxicology

Doses of 30 and 100 mg/kg (i.p.) (+)2-methylpiperidine and (−)2-methylpiperidine were well tolerated by male CD1 mice, and did not cause any deaths within 24 hours post-administration (Table 6). In contrast, 9.0 mg/kg (−)nicotine produced death in 4 out of 6 animals in addition to dyspnea and decreased activity, classic signs of cholinostimulation.

Importantly, (+)2-methylpiperidine did not potentiate the lethality elicited by i.p. administration of (−)nicotine. (Table 7).

TABLE 6

Lethality of (+)2-methylpiperidine or (−)2-methylpiperdine in mouse

|  | Deaths in 24 hours |
|---|---|
| (+)2-methylpiperidine |  |
| 30 mg/kg | 0/5 |
| 100 mg/kg | 0/5 |
| (−)2-methylpiperidine |  |
| 30 mg/kg | 0/5 |
| 100 mg/kg | 0/5 |

Compounds were given as the respective mandelic acid salts.

TABLE 7

Effects of Saline, (+)2-methylpiperidine, or (+)2-methylpiperdine on (−)nicotine induced mouse lethality

| (−)nicotine {mg/kg}: | DEATHS/24 hours | | | LD$_{50}$[95% C.I.] |
|---|---|---|---|---|
|  | 3 | 6 | 9 |  |
| Pretreatment |  |  |  |  |
| Saline | 0/6 | 2/8 | 4/6 | 7.7 [6.0–9.9] |
| (+)2-methylpiperidine |  |  |  |  |
| 0.1 mg/kg | 0/6 | 1/6 | 2/6 | 11.1 [5.8–21] |
| 10.0 mg/kg | 0/6 | 1/8 | 3/6 | 9.2 [5.8.14.5] |
| (−)2-methylpiperidine |  |  |  |  |
| 10.0 mg/kg | 0/6 | 0/6 | 4/6 | 7.7 [6.0–9.9] |

These data support the idea that (+)2-methylpiperidine is safe relative to (−)nicotine. Moreover, in contrast to its potentiation of the beneficial actions of (−)nicotine, it does not potentiate (−)nicotine induced acute lethality.

The compounds of the present invention may be used in the form of salts derived from inorganic or organic acids. These salts include but are not limited to the following: acetate, adipate, alginate, ascorbate, aspartate, benzoate, benzenesulfonate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, fumarate, hydrochloride, hydrobromide, hydroiodide, 2-hydroxy-ethanesulfonate, lactobionate, lactate, laurate, lauryl sulfate, maleate, methanesulfonate, nicotinate, 2-naphthalenesulfonate, oleate, oxalate, pamoate, palmitate, pectinate, persulfate, 3-phenylpropionate, phosphate, picrate, pivalate, propionate, stearate, succinate, sulfate, tartrate, thiocyanate, toluenesulfonate, undecanoate valerate salts and the like. Also, the basic nitrogen-containing groups may be quaternized with such agents as loweralkyl halides, including methyl, ethyl, propyl, and butyl chlorides, bromides, and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenylethyl bromides, and others. Water- or oil-soluble or dispersible products are thereby obtained.

The pharmaceutically-acceptable salts of the present invention can be synthesized from the compounds of formula (I) by conventional chemical methods. Generally, the salts are prepared by reacting the free amine with stoichiometric amounts or with an excess of the desired salt-forming inorganic or organic acid in a suitable solvent or various combinations of solvents.

The present invention includes one or more of the compounds of Formula (I) formulated into compositions together with one or more non-toxic pharmaceutically acceptable carriers, adjuvants or vehicles, which are collectively referred to herein as carriers, for parenteral injection, for oral administration in solid or liquid form, for rectal administration, and the like.

In order to reduce unwanted peripherally mediated side-effects, it is advantageous to incorporate into the composition a peripherally acting anti-cholinergic or anti-muscarinic agent such as N-methylscopolamine, N-methylatropine, propantheline, methantheline, or glycopyrrolate.

Compositions suitable for parenteral injection may comprise pharmaceutically-acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycos, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which may be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservative, buffers or propellants as may be required. Ophthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposones can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p 33 et seq.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to 100 mg/kg body weight daily and preferably 0.01 to 10 mg/kg/day. Dosage unit compositions may contain such amounts of submultiples thereof to make up the daily dose. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for treating a CNS disorder caused by a malfunction of the cholinergic system by administering to a host in need of such treatment a therapeutically-effective amount of (+) 2-methylpiperidine or a pharmaceutically-acceptable acid addition salt thereof.

2. A method according to claim 1 wherein a nicotinic agonist is administered with (+) 2-methylpiperidine and the therapeutically-effective amount of (+) 2-methylpiperidine in from 0.01 to 10 mg/kg/day.

3. A method according to claim 1 wherein the CNS disorder is dementia, anxiety, psychosis, stroke, attentional deficits or withdrawal from addictive substances.

4. A method according to claim 2, wherein the nicotinic agonist is (−) nicotine.

5. A method for modulating cortical cholinergic neurotransmission comprising administering to a host in need of such treatment a therapeutically-effective amount of (+) 2-methylpiperidine or a pharmaceutically-acceptable acid addition salt thereof.

* * * * *